(12) United States Patent
Park et al.

(10) Patent No.: US 7,192,760 B2
(45) Date of Patent: Mar. 20, 2007

(54) MICROORGANISMS AND PROCESSES FOR PRODUCING L-GLUTAMINE

(75) Inventors: Sung-Sik Park, Seoul (KR); Seung-Hyun Suh, Kyunggi-do (KR); Keun-Chul Lee, Kyunggi-do (KR); Dong-Woo Lee, Kyunggi-do (KR); Cheon-Ju Kim, Kyunggi-do (KR); Sang-Cheol Jeong, Kyunggi-do (KR)

(73) Assignee: Cheil Jedang Corporation (KR)

( * ) Notice: Subject to any disclaimer, the term of this patent is extended or adjusted under 35 U.S.C. 154(b) by 0 days.

(21) Appl. No.: 11/182,446

(22) Filed: Jul. 15, 2005

(65) Prior Publication Data

US 2005/0250187 A1    Nov. 10, 2005

Related U.S. Application Data

(63) Continuation of application No. 10/198,274, filed on Jul. 17, 2002, now Pat. No. 6,984,506, which is a continuation of application No. PCT/KR01/01952, filed on Nov. 15, 2001.

(30) Foreign Application Priority Data

Nov. 17, 2000  (KR)  ............................... 2000-68284
Nov. 17, 2000  (KR)  ............................... 2000-68285

(51) Int. Cl.
   *C12N 1/20*  (2006.01)
(52) U.S. Cl. ............. 435/252.1; 435/110; 435/252.32; 435/840

(58) Field of Classification Search ............. 435/252.1, 435/252.32, 840, 110
See application file for complete search history.

(56) References Cited

U.S. PATENT DOCUMENTS

| 3,886,039 | A | | 5/1975 | Yoshinaga et al. |
| 4,411,991 | A | * | 10/1983 | Hirakawa et al. ............. 435/42 |
| 5,521,074 | A | * | 5/1996 | Katsumata et al. ......... 435/115 |
| 6,962,805 | B2 | * | 11/2005 | Asakura et al. ............. 435/110 |
| 6,984,506 | B2 | * | 1/2006 | Park et al. .................. 435/110 |
| 2002/0137150 | A1 | * | 9/2002 | Ohtaki et al. ............... 435/110 |
| 2003/0096380 | A1 | * | 5/2003 | Park et al. .................. 435/110 |
| 2004/0152175 | A1 | * | 8/2004 | Nakamura et al. .......... 435/110 |

FOREIGN PATENT DOCUMENTS

| EP | 0379903 | 8/1990 |
| JP | 53-17675 | 12/1972 |
| JP | 54-062388 | 5/1979 |
| JP | 55-148094 | 11/1980 |
| JP | 56164792 | 12/1981 |
| JP | 60248195 | 12/1985 |
| JP | 02-186994 | 7/1990 |
| JP | 04-088994 | 3/1992 |
| KR | 91-8127 | 5/1991 |

* cited by examiner

*Primary Examiner*—Herbert J. Lilling
(74) *Attorney, Agent, or Firm*—Arent Fox PLLC

(57) ABSTRACT

The present invention provides novel microorganisms, *Brevibacterium lactofermentum* CJJA21 (Accession No. KCCM-10222), which is resistant to sodium azide, and *Brevibacterium lactofermentum* CJJA22 (Accession No. KCCM-10223), which is resistant to α-aminobutyric acid. These microorganisms are capable of producing L-glutamine in a higher yield than the known strains. The present invention further provides processes for producing L-glutamine using the microorganisms of the invention.

4 Claims, No Drawings

MICROORGANISMS AND PROCESSES FOR PRODUCING L-GLUTAMINE

CROSS-REFERENCE TO RELATED APPLICATION

This application is a continuation of application Ser. No. 10/198,274 filed Jul. 17, 2002, now U.S. Pat. No. 6,984,506 which in turn is a continuation application of International Application Ser. No. PCT/KR01/01952 filed Nov. 15, 2001 and published as WO 02/40643, which claims priority to Korean Application Ser. No. 2000/68284 and Korean Application Ser. No. 2000/68285, both filed Nov. 17, 2000. Said applications are included herein in their entirety by reference.

BACKGROUND

L-glutamine is an amino acid widely used as medicines such as therapeutic agents of gastroenterologic disorders, potentiators of liver and brain functions, immuno-enhancement agents, and therapeutic agents of gastric ulcer and alcoholism, etc., cosmetics such as moisturizers, etc., and health foods such as sports nutrients and nutrients for patients, etc.

According to the prior art, L-glutamine was obtained from sulfaguanidine-resistant strains (Japanese Patent, Laid-Open No. Sho53-17675), azaserine-resistant strains (Japanese Patent Laid-Open No. Sho55-148094) penicillin-sensitive strains (Japanese Patent Laid-Open No. Hei04-088994), tyrosine-glutamic acid (tyr-glu)-resistant strains (Japanese Patent Laid-Open No. Hei02-186994) and the like.

SUMMARY OF THE INVENTION

The present invention relates to novel microorganisms producing L-glutamine and to processes for producing L-glutamine using the same. More specifically, the invention relates to *Brevibacterium lactofermentum* CJJA21 (KCCM-10222) resistant to sodium azide and *Brevibacterium lactofermentum* CJJA22 (KCCM-10223) resistant to D,L-α-amino-n-butyric acid: α-ABA), both of which are capable of producing L-glutamine in a higher yield than the known strains, and to processes for producing L-glutamine using the same.

DETAILED DESCRIPTION OF THE INVENTION

The present inventors performed extensive studies to develop novel strains, which are capable of producing L-glutamine in a high productivity. We contemplated that strains resistant to sodium azide, a respiratory inhibitor, or to α-aminobutyric acid, an analogue of an amino acid, isoleucine, would have the increased productivity of L-glutamine. Thus, we screened sodium azide or α-aminobutyric acid-resistant strains from an original strain *Brevibacterium lactofermentum* KFCC-10680 (Korean Patent Publication No. 91-7818). This strain was deposited as KFCC-10680 with the Korean Culture Center of Microorganisms on Oct. 8, 1989 for the purpose of patent procedures and described in Korean Patent No. 91-7818, issued on Oct. 2, 1991. As a result, we identified that the sodium azide resistant strain *Brevibacterium lactofermentum* CJJA21 strain KCCM-10222 or α-aminobutyric acid-resistant strain *Brevibacterium lactofermentum* CJJA21 strain KCCM-102232 produce L-glutamine in a higher yield than the known strains and thus, completes the present invention. The strains are high GC content, gram-negative cubacteria, which are non-sporeforming and are non-pathogenic. The strains are cysteine-demanding and aerobic, with an optimum temperature for cultivation of 30° C. and an optimum pH of 6.8.

The present invention provides microorganisms producing L-glutamine and processes for producing L-glutamine using the same. The microorganisms according to the present invention are *Brevibacterium lactofermentum* CJJA21 (KCCM-10222) having a resistance to sodium azide and *Brevibacterium lactofermentum* CJJA22 (KCCM-10223) having a resistance to α-aminobutyric acid, both of which produce L-glutamine in a high yield. Further, the processes for producing L-glutamine according to the present invention is characterized by the activation of *Brevibacterium lactofermentum* CJJA21 or *Brevibacterium lactofermentum* CJJA22 followed by the cultivation of the activated strains.

In the present invention, mutants were induced by the following methods. *Brevibacterium lactofermentum* KFCC-10680 was treated with N-methyl-N'-nitro-N-nitrosoguanidine (NTG), a conventional mutagen and then, spread on a minimal medium (Medium 1) containing 500 mg/l of sodium azide thereby to obtain strains having a resistance to 500 mg/l of sodium azide.

More specifically, *Brevibacterium lactofermentum* KFCC-10680, which had been previously activated by cultivation on an activation medium (Medium 2) for 16 hours, was cultivated for 14 hours on a seed medium (Medium 3) sterilized at 121° C. for 15 minutes. Then, 5 mL of the culture medium was washed with 100 mM citrate buffer and thereto was added NTG at a final concentration of 200 mg/l. After 20 minutes, the medium was washed with 100 mM phosphate buffer. The strains treated with NTG were spread on a minimal medium (Medium 1) and the death rate was measured. As a result, the death rate was 85%.

In order to obtain sodium azide-resistant mutants, the NTG-treated strains were spread on a minimal medium (Medium 1) containing sodium azide at a final concentration of 500 mg/l and then, cultivated at 30° C. for 6 days to obtain sodium azide-resistant strains. The obtained resistant mutants were cultivated in a shaking Erlenmeyer flask containing a glutamine production medium (Medium 4) for 72 hours thereby to select a sodium azide-resistant strain producing L-glutamine in a 10% or more higher yield than the original strain, *Brevibacterium lactofermentum* KFCC-10680. The obtained strain was designated as CJJA21. *Brevibacterium lactofermentum* CJJA21 was deposited under the Budapest Treaty to the Korean Culture Center of Microorganisms whose address is Hongje-dong, Seodaemun-gu, Seoul, on Oct. 20, 2000, with the Accession No. KCCM-10222.

In addition, *Brevibacterium lactofermentum* KFCC-10680 was activated and cultivated in the substantially same manner as above. It was subsequently treated with NTG in the substantially same manner as above. In order to obtain α-aminobutyric acid-resistant mutants, the NTG treated strains were spread on a minimal medium (Medium 1) containing α-aminobutyric acid at a final concentration of 15 g/l and then, cultivated at 30° C. for 6 days to obtain α-aminobutyric acid-resistant strains. The obtained resistant mutants were cultivated in a shaking Erlenmeyer flask containing a glutamine production medium (Medium 4) for 72 hours thereby to select a α-aminobutyric acid-resistant strain producing L-glutamine in a 10% or more higher yield than the original strain, *Brevibacterium lactofermentum* KFCC-10680. The obtained strain was designated as CJJA22. *Brevibactertium lactofermentum* CJJA22 was deposited under the Budapest Treaty to the Korean Culture Center of Microorganisms whose address is Hongje-dong, Seodaemun-gu, Seoul, on Oct. 20, 2000, with the Accession No. KCCM-10223.

Culture media employed in the present invention have the following compositions:

Medium 1: Minimal medium

Glucose 1.0%, Ammonium Sulfate (($NH_4$)$_2SO_4$) 0.4%, Magnesium Sulfate ($MgSO_4$. $7H_2O$) 0.04%, Potassium Dihydrogen Phosphate ($KH_2PO_4$) 0.1%, Urea 0.1%, Thiamine HCl 0.0001%, Biotin 200 µg/l, Agar, pH 7.0

Medium 2: Activation medium

Beef extract 1%, Polypeptone 1%, Sodium Chloride (NaCl) 0.5%, Yeast Extract 0.5%, Agar 2%, pH 7.2

Medium 3: Seed medium

Glucose 5%, Bactgpeptone 1%, Sodium Chloride ($NH_4Cl$) 0.25%, Yeast Extract 1%, Biotin 3 µg/l, Urea 0.4%, pH 7.0

Medium 4: Glutamine production medium

Glucose 4.0%, Ammonium Chloride ($NH_4Cl$) 3.0%, Soy Protein Acid Hydrolyzate 0.3%, Calcium Carbonate ($CaCO_3$) 5%, Calcium Chloride ($CaCl_2$) 0.1%, Magnesium Sulfate ($MgSO_4.7H_2O$) 0.05%, Potassium Dihydrogen Phosphate ($KH_2PO_4$) 0.15%, Potassium Monohydrogen Phosphate ($K_2HPO_4$) 0.15%, Urea 0.3%, Thiamine, HCl 2 mg/l, Biotin 5 µg/l, Ferric Sulfate ($FeSO_4.7H_2O$) 20 mg/l, Manganese Sulfate ($MnSO_4.H_2O$) 20 mg/l, Zinc Sulfate ($ZnSO_4.7H_2O$) 12 mg/l, pH 6.8.

Sodium azide-resistance of *Brevibacterium lactofermentum* CJJA21 is shown in the following Table 1-1.

TABLE 1-1

| Strain | Sodium azide concentration (mg/l) | | | | | |
|---|---|---|---|---|---|---|
| | 0 | 100 | 200 | 300 | 500 | 800 |
| KFCC-10680 | +++ | + | + | − | − | − |
| CJJA21 | +++ | +++ | +++ | +++ | ++ | − |

+: growth,
−: no growth, cultivation at 30° C. for 6 days

α-Aminobutyric acid-resistance of *Brevibacterium lactofermentum* CJJA22 is shown in Table 1-2.

TABLE 1-2

| Strain | α-aminobutyric acid concentration (g/l) | | | | | |
|---|---|---|---|---|---|---|
| | 0 | 1 | 5 | 10 | 15 | 20 |
| KFCC-10680 | +++ | ++ | + | − | − | − |
| CJJA21 | +++ | +++ | +++ | +++ | ++ | − |

+: growth,
−: no growth, cultivation at 30° C. for 6 days

According to the present invention, L-glutamine can be obtained in a higher yield than the prior art. In some embodiments of the invention, about 10% more L-glutamine, more preferably about 15% more L-glutamine is produced by microorganisms of the invention than by wild-type strains grown under the same conditions. This improvement is illustrated by, inter alia, Examples 1–4. The obtained L-glutamine is useful for medicines such as therapeutic agents of gastroenterologic disorders, potentiators of liver and brain functions, immuno-enhancement agents, therapeutic agents of gastric ulcer and alcoholism, etc., cosmetics such as moisturizers, etc., and health foods such as sports nutrients and nutrients for patients, etc.

EXAMPLES

This invention will be better understood from the following examples. However, one skilled in the art will readily appreciate the specific materials and results described are merely illustrative of, and are not intended to, nor should be intended to, limit the invention as described more fully in the claims which follows thereafter.

Example 1

Strain: *Brevibacterium lactofermentum* CJJA21 Strain KCCM-10222

Fermentation Medium: Glucose 4.0%, Ammonium Chloride ($NH_4Cl$) 3.0%, Soy Protein Acid Hydrolyzate 0.3%, Calcium Carbonate ($CaCO_3$) 5%, Calcium Chloride ($CaCl_2$) 0.1%, Magnesium Sulfate ($MgSO_4.7H_2O$) 0.05%, Potassium Dihydrogen Phosphate ($KH_2PO_4$) 0.15%, Potassium Monohydrogen Phosphate ($K_2HPO_4$) 0.15%, Urea 0.3%, Thiamine, HCl 2 mg/l, Biotin 5 µg/l, Ferric Sulfate ($FeSO_4.7H_2O$) 20 mg/l, Manganese Sulfate ($MnSO_4.H_2O$) 20 mg/l, Zinc Sulfate ($ZnSO_4.7H_2O$) 12 mg/l, pH 6.8 (the same as Medium 4).

Fermentation procedure and result: To a shaking Erlenmeyer flask of 250 mL was injected 20 mL of the fermentation medium. The medium was sterilized at 121° C. for 15 minutes. Thereto was inoculated 1 loopfull of strains activated by the cultivation on an activation medium (Medium 2) at 30° C. for 16 hours and then, cultivated while shaking at 30° C. for 48 hours. The L-glutamine concentration of the fermented broth is shown in Table 2.

TABLE 2

| | KFCC-10680 (Original Strain) | CJJA21 (Variant) |
|---|---|---|
| Concentration of glutamine (g/l) | 12.6 | 14.5 |

Example 2

Strain: *Brevibacterium lactofermentum* CJJA21 Strain KCCM-10222

Fermentation medium: Glucose 10%, Ammonium Chloride ($NH_4Cl$) 4.5%, Soy Protein Acid Hydrolyzate 0.5%, Calcium Carbonate ($CaCO_3$) 5%, Calcium Chloride ($CaCl_2$) 0.1%, Magnesium Sulfate ($MgSO_4.7H_2O$) 0.05%, Potassium Dihydrogen Phosphate ($KH_2HPO_4$) 0.15%, Potassium Monohydrogen Phosphate ($K_2HPO_4$) 0.15%, Urea 0.3%, Thiamin (Thiamine.HCl) 2 mg/l, Biotin 5 µg/l, Ferric Sulfate ($FeSO_4.7H_2O$) 20 mg/l, Manganese Sulfate ($MnSO_4.H_2O$) 20 mg/l, Zinc Sulfate ($ZnSO_4.7H_2O$) 12 mg/l, pH 6.8.

Fermentation procedure and result: To a shaking Erlenmeyer flask of 250 mL was injected 20 mL of the fermentation medium. The medium was sterilized at 121° C. for 15 minutes. Thereto was inoculated 1 loopfull of strains activated by the cultivation on an activation medium (Medium 2) at 30° C. for 16 hours and then, cultivated while shaking at 30° C. for 72 hours. The L-glutamine concentration of the fermented broth is shown in Table 3.

TABLE 3

| | KFCC-10680 (Original Strain) | CJJA21 (Variant) |
|---|---|---|
| Concentration of glutamine (g/l) | 31.5 | 37.1 |

As shown in Table 3, *Brevibacterium lactofermentum* CJJA21 of the present invention produced L-glutamine in a 10% or more higher yield than the original strain, *Brevibacterium lactofermentum* KFCC-10680.

Example 3

*Brevibacterium lactofermentum* CJJA22 strain KCCM-10223 was cultivated according to the substantially same method as in Example 1. The L-glutamine concentration of the fermented broth is shown in Table 4.

TABLE 4

| | K-FCC-10680 (Original Strain) | CJJA22 (Variant) |
|---|---|---|
| Concentration of glutamine (g/l) | 12.4 | 14.1 |

Example 4

*Brevibacterium lactofermentum* CJJA22 strain KCCM-10223 was cultivated according to the substantially same method as in Example 2. The L-glutamine concentration of the fermented broth is shown in Table 5.

TABLE 5

| | KFCC-10680 (Original Strain) | CJJA22 (Variant) |
|---|---|---|
| Concentration of glutamine (g/l) | 31.1 | 36.5 |

What is claimed is:

1. Isolated *Brevibacterium lactofermentum* CJJA21 strain KCCM-10222.

2. The isolated *Brevibacterium lactofermentum* CJJA21 strain of claim 1 wherein said strain is resistant to sodium azide.

3. Isolated *Brevibacterium lactofermentum* CJJA22 strain KCCM-10223.

4. The isolated *Brevibacterium lactofermentum* CJJA22 strain of claim 3 wherein said strain is resistant to α-aminobutyric acid.

* * * * *